United States Patent
Kennett et al.

(10) Patent No.: US 8,726,747 B2
(45) Date of Patent: May 20, 2014

(54) SAMPLING VESSEL FOR FLUIDIZED SOLIDS

(75) Inventors: Richard Douglas Kennett, Boyle (CA); Iftikhar Huq, Edmonton (CA); Daniel Bulbuc, Fort McMurray (CA); David Dennis Famulak, Sherwood Park (CA); Jacqueline Hess, Fort McMurray (CA); Christian Schroeter, Edmonton (CA)

(73) Assignee: Syncrude Canada Ltd., Calgary (CA), In trust for the owners of the Syncrude Project as such owners exist now and in the future ( * ) Notice: Subject to any disclaimer, the term of this patent is extended or adjusted under 35 U.S.C. 154(b) by 514 days.

(21) Appl. No.: 12/765,679

(22) Filed: Apr. 22, 2010

(65) Prior Publication Data

US 2010/0269599 A1    Oct. 28, 2010

Related U.S. Application Data

(60) Provisional application No. 61/172,107, filed on Apr. 23, 2009.

(51) Int. Cl.
*G01N 1/20* (2006.01)

(52) U.S. Cl.
USPC .................. 73/864.51; 73/863.11; 73/863.41; 73/863.51; 73/863.81

(58) Field of Classification Search
USPC .................... 73/863, 863.11, 863.41, 863.42, 73/863.51, 863.81, 864, 864.33, 864.51
See application file for complete search history.

(56) References Cited

U.S. PATENT DOCUMENTS

| | | | |
|---|---|---|---|
| 2,687,992 A | | 8/1954 | Leffer |
| 2,874,095 A | * | 2/1959 | Boisture et al. ............... 208/127 |
| 2,881,130 A | | 4/1959 | Pfeiffer et al. |
| 2,885,338 A | * | 5/1959 | Evans ........................... 208/409 |
| 3,130,584 A | * | 4/1964 | Kennedy ....................... 374/110 |
| 3,133,444 A | * | 5/1964 | Karwat ....................... 73/863.12 |
| 3,250,128 A | * | 5/1966 | Cassel ........................ 73/863.51 |
| 3,260,120 A | * | 7/1966 | Stilwell ...................... 73/863.54 |
| 3,290,119 A | * | 12/1966 | Lewis et al. ..................... 422/86 |
| 3,457,788 A | * | 7/1969 | Miyajima .................. 73/863.21 |
| 3,473,388 A | * | 10/1969 | Lynn .......................... 73/863.03 |
| 3,487,695 A | * | 1/1970 | Ellis et al. .................. 73/863.81 |
| 3,614,230 A | * | 10/1971 | Crawford ........................ 356/36 |
| 3,659,461 A | * | 5/1972 | Thompson .................. 73/863.54 |
| 3,786,682 A | * | 1/1974 | Winter et al. ............. 73/863.86 |
| 3,803,921 A | * | 4/1974 | Dieterich ........................ 73/203 |
| 3,881,359 A | * | 5/1975 | Culbertson ................ 73/863.12 |
| 3,921,458 A | * | 11/1975 | Logan ........................ 73/863.58 |
| 3,973,440 A | * | 8/1976 | Vande Ven et al. ........ 73/863.81 |

(Continued)

FOREIGN PATENT DOCUMENTS

EP          0102828 A2 *  3/1984

*Primary Examiner* — David A Rogers
(74) *Attorney, Agent, or Firm* — Bennett Jones LLP

(57) ABSTRACT

A method, apparatus and system for obtaining a sample of a fluid solids, such as a coke and hydrocarbon mixture, from a fluid solids process is provided. A sample vessel is provided that contains a first end, a second end, an aperture in the first end and an interior cavity. A cooling device can be provided for cooling material in the interior cavity of the sampling vessel. In operation, fluid solids can be routed through the aperture and collected in the interior cavity. The collected sample material can then be cooled by the cooling device and used for testing.

19 Claims, 2 Drawing Sheets

(56) References Cited

U.S. PATENT DOCUMENTS

| | | | |
|---|---|---|---|
| 4,169,041 A | 9/1979 | Schuette | |
| 4,195,491 A * | 4/1980 | Roncaglione | 62/384 |
| 4,236,897 A * | 12/1980 | Johnston | 44/530 |
| 4,353,260 A * | 10/1982 | Round | 73/863.41 |
| 4,383,438 A * | 5/1983 | Eaton | 73/61.62 |
| 4,481,833 A * | 11/1984 | Bajek | 73/863.21 |
| 4,587,856 A * | 5/1986 | Otis | 73/863.51 |
| 4,637,266 A * | 1/1987 | Greenwood | 73/863.86 |
| 4,653,335 A * | 3/1987 | Orlando | 73/863.85 |
| 4,703,661 A * | 11/1987 | Evers | 73/861.66 |
| 4,876,901 A * | 10/1989 | Campbell | 73/863 |
| 4,942,774 A * | 7/1990 | McFarland | 73/864.81 |
| 4,958,527 A * | 9/1990 | Couvillion | 73/863.86 |
| 4,974,455 A * | 12/1990 | McGowan et al. | 73/863.12 |
| 5,104,519 A * | 4/1992 | Haddad et al. | 208/152 |
| 5,130,012 A * | 7/1992 | Edwards et al. | 208/113 |
| 5,237,881 A * | 8/1993 | Ross | 73/863.12 |
| 5,363,707 A * | 11/1994 | Augenblick et al. | 73/864.84 |
| 5,373,724 A * | 12/1994 | Lau et al. | 73/23.2 |
| 5,501,080 A * | 3/1996 | McManus et al. | 62/55.5 |
| 5,588,988 A * | 12/1996 | Gerstel et al. | 96/101 |
| 5,648,603 A * | 7/1997 | Hanson | 73/152.02 |
| 5,759,482 A * | 6/1998 | Gregory et al. | 266/79 |
| 6,021,678 A * | 2/2000 | Vardiman et al. | 73/863.11 |
| 6,658,876 B1 * | 12/2003 | Richardson et al. | 62/201 |
| 6,694,796 B2 * | 2/2004 | Juneau et al. | 73/1.03 |
| 6,843,103 B2 * | 1/2005 | Aguilera et al. | 73/28.01 |
| 7,168,332 B2 * | 1/2007 | Orange et al. | 73/863.44 |
| 7,253,005 B2 * | 8/2007 | Coute et al. | 436/174 |
| 7,299,709 B1 * | 11/2007 | Grove et al. | 73/863.11 |
| 7,422,627 B2 * | 9/2008 | Wetzig | 96/4 |
| 7,472,612 B2 * | 1/2009 | Zaromb et al. | 73/863.21 |
| RE41,319 E * | 5/2010 | Bradley et al. | 73/864.33 |
| 7,730,796 B2 * | 6/2010 | Shimada et al. | 73/863.83 |
| 2002/0166365 A1 * | 11/2002 | Kogure et al. | 73/28.01 |
| 2003/0205098 A1 * | 11/2003 | Kalidindi | 73/863.81 |
| 2004/0159167 A1 * | 8/2004 | Bremer et al. | 73/864.85 |
| 2005/0047965 A1 * | 3/2005 | Coute et al. | 422/99 |
| 2008/0135456 A1 | 6/2008 | Siskin et al. | |
| 2008/0148871 A1 * | 6/2008 | Himes et al. | 73/863.81 |
| 2008/0190178 A1 * | 8/2008 | Hammami et al. | 73/54.01 |
| 2008/0190218 A1 * | 8/2008 | Riazanskaia et al. | 73/864 |
| 2008/0202261 A1 * | 8/2008 | Felix et al. | 73/863.23 |
| 2010/0011843 A1 * | 1/2010 | Smith et al. | 73/61.71 |
| 2010/0186523 A1 * | 7/2010 | Vesala | 73/863.11 |

\* cited by examiner

//SAMPLING VESSEL FOR FLUIDIZED SOLIDS

CROSS REFERENCE TO RELATED APPLICATIONS

The present application claims priority under 35 U.S.C. §119(e) to U.S. provisional patent application No. 61/172,107 filed Apr. 23, 2009.

FIELD OF THE INVENTION

The present invention relates to a method and apparatus for obtaining a sample of fluid solids used in fluid solids processes and, more particularly, a method and apparatus for obtaining such a sample in a manner whereby further reactions in the sample caused by heat are reduced.

BACKGROUND OF THE INVENTION

Continuous fluid solids processes, such as fluidized coking of hydrocarbons, are used in many industrial processes. For example, heavy hydrocarbons are sometimes treated by a coking process to thermally crack and separate the hydrocarbon into lighter, more desirable components. Some of these coking processes are done using a continuous fluid coking process. In these processes, it is often desirable to obtain samples of the fluid solids to determine how the process is operating, to optimize variables in the process such as heat, to diagnosis of problems with a process, etc. However, obtaining such a sample is usually not just a straightforward process of obtaining some of the fluid solids.

For example, in a fluid coking process for hydrocarbons, typically a reactor or coker containing fluidized hot coke particles is used to treat an incoming feed of hydrocarbon. The hydrocarbon introduced into the coker is thermally cracked by the heat provided by the hot coke and more desirable components of the hydrocarbon are separated out. Typically, the coker is operated at a temperature of about 530° C. Coke particles formed during the process are generally coated with residual hydrocarbons and are therefore removed from the coker to a heater or burner where the coke particles are heated to remove this hydrocarbon coating. A portion of the coke particles heated in the burner are then recirculated back to the coker.

The coke that is heated in the burner is typically heated to 550° C. or more before it is transported back to the reactor vessel (coker). The heated coke is then passed back into the reactor where, with the addition of steam, a bed of fluidized coke is formed in the reactor. In operation, a feed, such as a heavy hydrocarbon like bitumen, is introduced into the reactor and placed in contact with the bed of fluidized coke. The heat from the heated coke causes some of the feed to be vaporized, while some of it is deposited on the coke particles and undergoes thermal cracking. This material on the coke particles cracks and vaporizes leaving a residue on the coke particles that dries to form coke. The coke particles used in the process will eventually form a number of layers like an onion, as hydrocarbon forms on the coke particles and forms more and more layers of coke.

During the fluid coking process, it is often desirable to obtain a sample of coke to determine the operating conditions in the reactor, burner, etc. However, the sample of the coke will typically be at an elevated temperature (i.e., greater than 500° C.) and will usually contain hydrocarbon. However, by withdrawing some of the hot coke into a sample container and letting it cool naturally, this can result in the coke sample to continue with the thermal cracking of any hydrocarbon present in the sample. This can result in the obtained sample having much different characteristics by the time it is tested than the sample that was originally collected.

SUMMARY OF THE INVENTION

In a first aspect, a method of obtaining a sample of a fluid solids from a fluid solids process is provided. The method comprises: providing a sample vessel having an interior cavity; collecting the sample material in the interior cavity of the sample vessel; and cooling the sample material in the interior cavity of the sample vessel.

In a second aspect, an apparatus for obtaining a sample of fluid solids from a fluid solids process is provided. The apparatus comprises: an interior cavity; a first end; a second end; an aperture in the first end of the apparatus leading into the interior cavity; and a cooling device for cooling material in the interior cavity.

In a third aspect, a system for obtaining a sample of fluid solids from a fluid solids process is provided. The system comprises: a sample vessel having an interior cavity, an aperture leading into the interior cavity, a cooling device for cooling material in the interior cavity and a vent conduit in fluid communication with the interior cavity; an incoming conduit connectable to the sample vessel to route sample material from a fluid solids process to the aperture of the sampling vessel; and a gas conduit connectable to the vent conduit of the sample vessel for routing gases away from the sampling vessel.

BRIEF DESCRIPTION OF THE DRAWINGS

Referring to the drawings wherein like reference numerals indicate similar parts throughout the several views, several aspects of the present invention are illustrated by way of example, and not by way of limitation, in detail in the figures, wherein.

DESCRIPTION OF VARIOUS EMBODIMENTS

The detailed description set forth below in connection with the appended drawings is intended as a description of various embodiments of the present invention and is not intended to represent the only embodiments contemplated by the inventor. The detailed description includes specific details for the purpose of providing a comprehensive understanding of the present invention. However, it will be apparent to those skilled in the art that the present invention may be practiced without these specific details.

Figure 1:
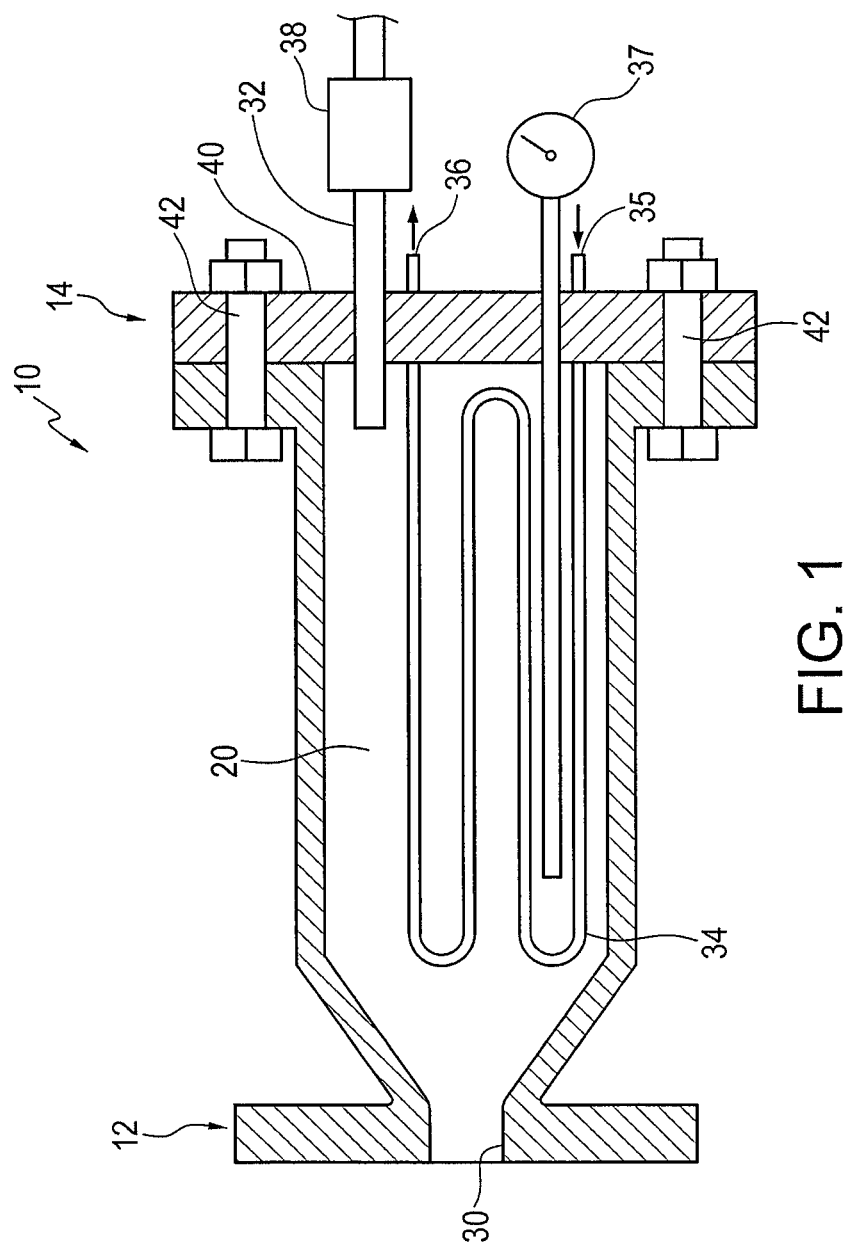
FIG. 1 is a schematic illustration of a sampling vessel.

FIG. 1 illustrates a sampling vessel 10 for use in obtaining a sample of fluidized solids such as fluidized coke. The sampling vessel 10 has a first end 12, a second end 14, and defines an interior cavity 20. Sample material collected by the sampling vessel 10 is collected in the interior cavity 20. An aperture 30 on the first end 12 of the sampling vessel 10 provides an inlet into the interior cavity 20. In one aspect, the cross sectional area of the interior cavity 20 may increase from the aperture 30 provided at the first end 12 of the sampling vessel 10 towards the second end 14 of the sampling vessel 10.

On the second end 14 of the sampling vessel 10 a lid 40 can be provided. The lid 40 can be securably attachable to the second end 14 of the sample vessel 10, such as by threaded fasteners 42, clamps or other like fasteners. The lid 40 can be used to enclose the interior cavity 20 when collecting the sample and may be removed from the second end 14 of the sample vessel 10 when it is necessary to gain access to the interior cavity 20 and sample material collected in the interior cavity 20.

A vent conduit 32 can be provided in fluid communication with the interior cavity 20 to allow gas to vent from the interior cavity 20 through the vent conduit 32. A filter 38 can be provided on the vent conduit 32 allowing gas/vapor to pass through the filter 38, thereby preventing substantial amounts of the sample material to pass by the filter 38. In one aspect, the filter 38 can be a 90 μm filter.

The sample vessel 10 further comprises a cooling device 34 for rapidly cooling the sample once it enters the vessel. For example, the cooling device 34 can be a cooling coil passing through the interior cavity 20. Using a coiling coil for the cooling device 34 allows a cooling fluid, such as water, Freon, alcohol, etc., to be routed through an inlet 35 of the coiling device 34, circulate through the portion of the cooling device 34 positioned in the interior cavity 20 of the sampling vessel 10 and cool the contents of the interior cavity 20 of the sampling vessel 10 before the cooling fluid exits through an outlet 36 of the cooling device 34. In an aspect, the cooling device 34 can be a cooling coil that takes a circuitous path through the interior cavity 20 allowing more sample material in the interior cavity 20 to come into contact with the cooling device 34.

A thermometer 37 can be provided passing into the interior cavity 20 of the sampling vessel 10 to take temperature readings of the interior cavity 20 and thus the sample material collected in the interior cavity 20 of the sampling vessel 10.

In operation, to obtain a sample of fluidized solids, such as fluidized coke, the material to be sampled is collected in the sampling vessel 10 by allowing it to pass through the aperture 30 into the interior cavity 20. As the sample material enters the interior cavity 20 the displaced gas/vapor in the interior cavity 20 can escape through the venting conduit 32 in the second end 14 of the sampling vessel 10. Filter 38 usually plugs within a few seconds and prevents the sample (e.g., coke) from exiting the first end 12 of the sampling vessel 10.

While the sample material is flowing into the interior cavity 20 or shortly after the interior cavity 20 is filled with the sample material, the cooling device 34 can be used to cool the fluidized solids in the interior cavity 20 of the sampling vessel 10. If the cooling device 34 is a cooling coil, cooling fluid can be circulated through the coiling device 34 to cool the fluidized coke sample in the interior cavity 20 and reduce the effect of further reactions in the sample material (e.g., thermal cracking of hydrocarbons in/on the sample). The thermometer 37 allows an operator to monitor the temperature of the sample material in the sampling vessel 20 while the cooling device 34 is cooling the sample material in the interior cavity 20.

In this manner, the sample vessel 10 can reduce the effect of elevated temperatures on the sample material. For example, if the sample material is coke from a fluid coking process, the sample material can be obtained from various heights in the reactor, i.e., the top of the fluidized bed, in the stripper region, the bottom of the reactor, etc, it could also be obtained from the coke that is removed from the reactor and being routed to the burner, from the coke that is being routed from the burner back to the reactor, etc. In most cases, especially if the sample material is obtained from the coke bed in the reactor, the sample material will contain a mixture of coke and hydrocarbon. The sample material entering the sample vessel 10 can have an elevated temperature of 500° C. or, more typically, 530° C. Thermal cracking of hydrocarbon can occur at these high temperatures. Thus, it is desirable to rapidly cool the sample to a lower temperature, for example, to about 360° C. or lower. As long as the hydrocarbon has an elevated temperature, thermal cracking of hydrocarbon in the sample material can continue to occur changing the characteristics of the sample material. By using the sample vessel 10, more accurate sampling can be achieved by reducing or preventing additional thermal cracking of the hydrocarbons in the obtained sample material.

Figure 2:
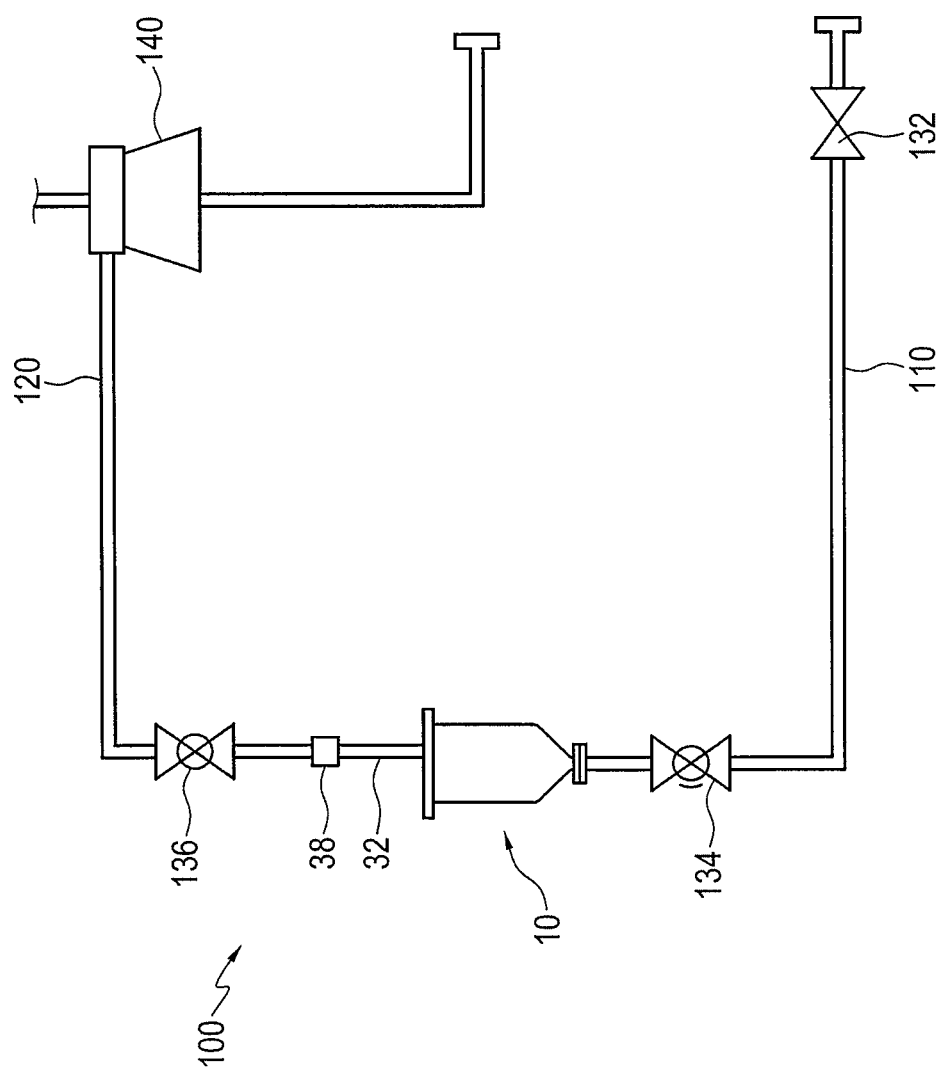
FIG. 2 is a schematic illustration of a sampling system incorporating the sampling vessel of FIG. 1.

FIG. 2 illustrates a sampling system 100 that incorporates the sampling vessel 10. The sample vessel 10 is connected to an incoming conduit 110 that routes sample material from a fluid solids process. The incoming conduit 110 can be connected to a source of sampling material and can route sample material from the source to the sample vessel 10. A gas conduit 120 can be provided to route gas vented from the sample vessel 10 to be properly disposed of/dealt with. The gas conduit 120 can be provided in fluid communication with the vent conduit 32 and the filter 38 to route gas vented from the interior cavity 20 of the sample vessel 10 away to be properly discharged/disposed of. An eductor 140 can be provided in line with gas conduit 120 to route vapors to be properly discharged. A number of valves, such as gate valves, ball valves, etc., can be provided to route the sample material through the sampling system 100. For example a first valve 132 can direct sample material into the sampling system 100, a second valve 134 can direct sample material into the sample vessel 10, a third valve 136 can direct gas through the gas conduit 120, etc.

The sampling system 100 can be connected to any point in a fluid solids process from which sample material is desired to be taken, with the incoming conduit 110 connected to the desired part of the system. For example, if the fluid solids process is a fluid coking process, the sampling system 100 can be operatively connected to various heights of the reactor, i.e. top of the fluid bed, bottom of the reactor, etc., it could also be connected to lines that convey coke from the reactor to the burner, from lines routing the coke back from the burner to the reactor, etc.

Referring to FIGS. 1 and 2, in operation, the first valve 132 and second valve 134 can be opened to route sample material through the incoming conduit 110 to sample vessel 10. At the sample vessel 10, the sample material passes through the aperture 30 of the sample vessel 10 and into the interior cavity 20 of the sample vessel 10. The third valve 136 can be opened to route gas out the sample vessel 10, through the vent conduit 32 and the filter 38 and through the gas conduit 120 to be routed away to be discharged. As sample material begins entering the sample vessel 10 or shortly after the sample material has entered the sample vessel 10, the cooling device 34 can be used to rapidly cool the sample material. If the cooling device 34 is a cooling coil, cooling fluid can be circulated through the cooling device 34 to cool the sample material. This cooling fluid can be circulated through the cooling device 34 until the sample material is cooled to a desired temperature. For example, if the sample material is from a fluid coking process and contains hydrocarbon, the desired temperature might be below a temperature where thermal cracking of hydrocarbons may occur, such as 360° C. or below. Once the sample material has been cooled to a desired temperature, the sample vessel 10 can be disconnected from the sampling system 100 and taken to a laboratory for testing.

The previous description of the disclosed embodiments is provided to enable any person skilled in the art to make or use the present invention. Various modifications to those embodiments will be readily apparent to those skilled in the art, and the generic principles defined herein may be applied to other embodiments without departing from the spirit or scope of the invention. Thus, the present invention is not intended to be limited to the embodiments shown herein, but is to be accorded the full scope consistent with the claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims. Moreover, nothing disclosed herein is intended to be dedicated to the public regardless of whether such disclosure is explicitly recited in the claims.

The invention claimed is:

1. A method of obtaining a sample comprising hydrocarbon and hot fluid solids from a fluid solids process, the method comprising:
   providing a sample vessel having an interior cavity;
   collecting the sample comprising hydrocarbon and hot fluid solids in the interior cavity of the sample vessel;
   cooling the sample comprising hydrocarbon and hot fluid solids while the sample is retained in the interior cavity of the sample vessel to reduce thermal cracking of the hydrocarbon present in the sample.

2. The method of claim 1 wherein the sample comprising hydrocarbon and hot fluid solids is cooled in the interior cavity of the sample vessel by providing a cooling coil running through the interior cavity and circulating cooling fluid through the cooling coil.

3. The method of claim 2 further comprising venting gas from the interior cavity of the sample vessel while the sample comprising hydrocarbon and hot fluid solids is being collected in the interior cavity.

4. The method of claim 3 wherein the fluid solids is a coke and the fluids solid process is a fluid coking process.

5. The method of claim 1 wherein a lid is provided on the sample vessel to allow access to the interior cavity.

6. An apparatus for obtaining a sample of fluid solids from a fluid solids process, the apparatus comprising:
   a sample vessel having an interior cavity, a first end, a second end, an aperture in the first end of the sample vessel leading into the interior cavity, and a cooling device comprising a cooling coil for cooling the interior cavity; and
   an incoming conduit connectable to a source of the sample and to the aperture in the first end of the sample vessel to route the sample from the source to the interior cavity for cooling.

7. The apparatus of claim 6 wherein the cooling coil takes a circuitous path through the interior cavity.

8. The apparatus of claim 6 further comprising a vent conduit in fluid communication with the interior cavity.

9. The apparatus of claim 8 further comprising a filter inline with the vent conduit to prevent substantial amounts of the fluid solids to pass by the filter.

10. The apparatus of claim 6 further comprising a thermometer passing into the interior cavity.

11. The apparatus of claim 6, wherein the second end of the apparatus comprises a removable lid to provide access to the interior cavity.

12. The apparatus of claim 11 further comprising a vent conduit provided in the lid and in fluid communication with the interior cavity.

13. The apparatus of claim 11 further comprising a thermometer passing through the lid and into the interior cavity.

14. A system for obtaining a sample comprising hydrocarbon and hot fluid solids from a fluid solids process, the system comprising:
   a sample vessel having an interior cavity, an aperture leading into the interior cavity, a cooling device for cooling the sample comprising hydrocarbon and hot fluid solids when it is contained in the interior cavity to reduce thermal cracking of the hydrocarbon present in the sample, and a vent conduit in fluid communication with the interior cavity;
   an incoming conduit connectable to the sample vessel to route the sample from the fluid solids process to the aperture of the sampling vessel;
   a gas conduit connectable to the vent conduit of the sample vessel for routing gases away from the sampling vessel; and
   a first valve to control the flow of the sample in the incoming conduit, a second valve to control the flow of the sample into the sampling vessel and a third valve to control the flow of gas from the sample vessel through the gas conduit.

15. The system of claim 14 wherein the cooling device is a cooling coil that takes a circuitous path through the interior cavity.

16. The system of claim 14 further comprising a filter inline with the vent conduit.

17. The system of claim 14 further comprising a thermometer passing into the interior cavity of the sample vessel.

18. The system of claim 14 further comprising an eductor inline with the gas conduit.

19. The system of claim 14 wherein the sample vessel can be disconnected from the incoming conduit and the gas conduit so that the sample vessel can be removed from the system.

* * * * *